United States Patent [19]

Smyth et al.

[11] Patent Number: 4,686,989

[45] Date of Patent: Aug. 18, 1987

[54] METHOD OF OPERATING PACEMAKER FOR DETECTING PACEMAKER-MEDIATED TACHYCARDIA

[75] Inventors: Nicholas P. D. Smyth, 5316 Portsmouth Rd., Spring Hill, Bethesda, Md. 20816; Bernard J. Stevens, Carrolltown, Pa.

[73] Assignee: Nicholas P. D. Smyth, Washington, D.C.

[21] Appl. No.: 734,842

[22] Filed: May 16, 1985

[51] Int. Cl.[4] ............................................. A61N 1/36
[52] U.S. Cl. ........................ 128/419 PG; 128/419 PT
[58] Field of Search .................... 128/419 PG, 419 PT

[56] References Cited

U.S. PATENT DOCUMENTS 4,554,920 11/1985 Baker, Jr. et al. ............ 128/419 PG
4,590,944 5/1986 Mann et al. .................. 128/419 PG

FOREIGN PATENT DOCUMENTS 87756 9/1983 European Pat. Off. ..... 128/419 PG

Primary Examiner—William E. Kamm

Attorney, Agent, or Firm—Hymen Diamond

[57] ABSTRACT

Pacer mediated tachycardia (PMT) is detected while the pacemaker is in the host and automatically suppressed and at the same time an indication that tachycardia has occurred and been suppressed is produced so that corrective action can be taken. The pacemaker, operating in the DDD mode, is monitored during operation. On the detection of PMT, the post ventricular atrial refractory period (PVARP) is automatically set and maintained at a magnitude, of 500 or 550 ms, substantially greater than the time of retrograde conduction from the ventricle to the atrium on the occurrence of a pulse in the ventricle. At the same time, the operation of the pacemaker is transferred from the DDD mode to the DDT mode. This transition provides an indication the PMT has occurred so that the physician can correct the operation of the pacemaker. Where PMT has occurred and been suppressed by lengthening the PVARP, the PVARP is reset to start timing out on the occurrence of a ventricular event. The minimum rate for the pacer is also increased by a small magnitude, 5.

13 Claims, 15 Drawing Figures

DDD PACING LADDER DIAGRAM

FIG.9 DDD PACING LADDER DIAGRAM

DDD PACING LADDER DIAGRAM

DDD PACING LADDER DIAGRAM

DDD PACING LADDER DIAGRAM

DDD PACING LADDER DIAGRAM
PMT TERMINATION BY INVENTION

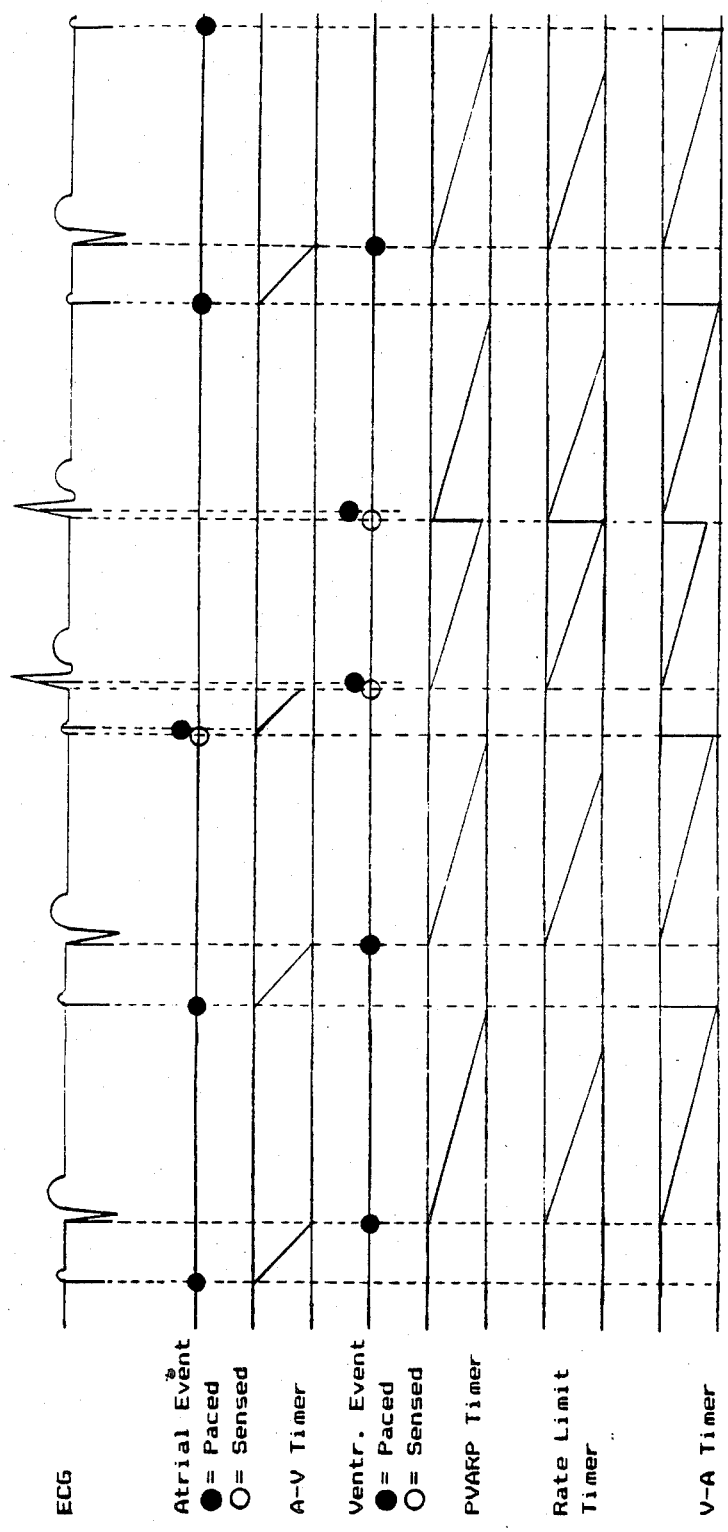

METHOD OF OPERATING PACEMAKER FOR DETECTING PACEMAKER-MEDIATED TACHYCARDIA

BACKGROUND OF THE INVENTION

This invention relates to the operation of heart pacemakers. It has particular relationship to operation of pacemakers having leads or electrodes both to the atrium and to the ventricle and operating in the DDD mode. During normal operation, the P wave is produced as a result of contraction of the atrium and a QRS wave as a result of contraction of the ventricle. The expression DDD is a code which identifies a mode of operation of pacemaker. Generally, D means double. The code DDD is part of a system of codes describing the operation of pacemakers which have been developed over a period of years. Among the publications dealing with these codes are Parsonnet, V., Furman, S., Smyth, N.P.D.: *Report of the Inter-Society Commission for Heart Disease Recourses—Implantable Cardiac Pacemakers: Status Report and Resource Guidelines,* American Journal of Cardiology, Vol. 34, pp. 487–500, Oct. 1974 and V. Parsonnet, S. Furman and N. P. D. Symth—*A Revised Code for Pacemaker Identification:* PACE, Vol. 4, pp. 400–402, July–August 1981. Victor Parsonnet Chairman, Seymour Furman, Nicholas P. D. Smyth, Michael Bilitch Members—*Report of Inter-Society Commission for Heart Disease Resources—Optional Resources for Implantable Pacemakers*—American Heart Association—*Circulation,* Vol. 68, pp. 227A–244A, July 1983. For the three-letter code, the first letter signifies what chamber is paced, the second what chamber is sensed for naturally occurring waves, and the third, the response of the pacemaker to the sensed wave; either triggered (T), inhibitory (I), or both (D).

With respect to the code DDD, the first D means that both chambers, the atrium and the ventricle, are paced, the second D means that both chambers are sensed for naturally-occurring or intrinsic waves and the third D means that the packemaker responds to the sensing by both triggered and inhibitory responses. If the pacemaker senses an intrinsic wave in the atrium, it triggers a pulse for the ventricle which is delivered after the atrio-ventricular (AV) delay. If, in the meantime, a ventricular wave is sensed, the ventricular pulse which was triggered in the atrium is inhibited in the ventricle. If an intrinsic atrial wave is not sensed, the pacemaker produces an atrial pulse and after the AV delay, the pacemaker produces a ventricular pulse. If, in this case, an intrinsic ventricular wave is sensed, the pacemaker pulse is inhibited. This may occur even for a wave occurring as a premature ventricular contraction (PVC).

The atrial or ventricular pulse from the pacemaker has the appearance in an ECG of a sharp line or spike and is frequently referred to herein as a "spike". Usually an intrinsic event will be referred to herein as a wave and the output signal to the heart of a pacemaker will be referred to herein as a spike or pulse. A spike to the atrium stimulates a P wave, a spike to the ventricle stimulates a QRS wave. A spike, a P wave or a QRS wave is sometime referred to herein as an event.

At this point, it appears desirable to discuss the frequency or period of heart beats and related intervals. The typical heart beat frequency in beats per minute of a person who is resting is about 70; the corresponding period is 857 ms. A person who is exerting himself, running or exercising vigorously, may have 160 heart beats per minute; the corresponding period is 375 ms. Pacemakers are normally programmed to operate at about 70 beats per minute. When an intrinsic atrial wave occurs, it triggers the pacemaker to produce a ventricular pulse which may be inhibited by the occurrence of an intrinsic ventricular wave. In the absense of intrinsic waves during an interval, the pacemaker would produce atrial pulses at the frequency for which it is programmed and ventricular pulses would be triggered after each AV delay. The AV delay is a pacemaker interval which is programmed. It ranges up to 250 ms, but is typically set in the range between 125 ms and 200 ms.

This invention concerns itself with pacer mediated tachycardia (PMT) which has complicated the application of physiological pacing in the DDD mode with a pacemaker which has leads both to the atrium and to the ventricle. A patient who encounters pacer mediated tachycardia experiences a rapid heat-beat, which not only causes the patient discomfort, but may also be hazardous.

The cause of PMT is retrograde conduction; i.e., conduction from the ventricle to the atrium (VA conduction). Of patients with complete antegrade atrio-ventricular (AV) block, about 30 to 40% have intact retrograde conduction. Of patients having intact; i.e., normal AV conduction, about 80 to 85% have intact retrograte; i.e., VA conduction. A patient may have intact AV conduction and may still require a pacemaker because his heart beat is at a low frequency. In a pacemaker operating in the DDD mode, a paced beat or an intrinsic beat in the atrium triggers a beat in the ventricle. These ventricular beats may generate a P wave in the atrium by retrograde conduction. More commonly, the P wave may be generated by retrograde conduction by the electrical pulse resulting from a premature ventricular contraction (PVC). The generation of the retrograde P wave by a paced pulse or normal intrinsic ventricular wave is less likely because when the paced pulse or normal intrinsic wave is generated, the retrograde conduction path may be closed, while when the PVC wave is generated, the path is open or is likely to be open. Essentially, the retrograde P wave is a feedback impulse. It causes the pacemaker to fire to the ventricle after a fixed or programmed AV delay. The resulting ventricular depolarization sends a retrograde impulse to the atrium repeating the pulsing similarly to the operation which takes place in a feedback oscillator. The resulting PMT usually causes the pacemaker, at once, to produce pulses at the upper rate limit of the pacemaker. This upper rate liimit is timed by an additional timer in the pacemaker maker which is progammable. It is dependent on the AV delay and on the post ventricular atrial refractory period (PVARP), and may have any magnitude from about 90 to 170 beats per minute. It limits the rate or frequency beats at which the pacemaker can operate. What happens is that after each excitation of a P wave by retrograte conduction, the high-frequency timer and the AV delay time out and when they have both timed out, a ventricular pulse is fired and the process is repeated. The high-frequency timer precludes pulsing at the periodicity of the AV delay which may exceed 300 pulses per minute. The resulting high beat frequency discomforts the patient and, in addition, subjects the patient to risk. The PMT may be stopped by fatigue in the retrograde path, or it may be stopped by application of a magnetic signal to convert the pacemaker to fixed pacing in the DOO mode, temporarily. In the DOO mode, both chambers are paced, but there is neither sensing of the chambers nor, in the absence of sensing, response of the pacemaker in either the triggered or inhibitory mode.

In accordance with the teachings of the prior art, PMT is precluded by elongating the postventricular-atrial refractory period (PVARP) for one period responsive to the sensing of a premature ventricular contraction (PVC). The PVARP is lengthened for only one period; i.e., the one after the PVC occurs. The refractory period is the period during which the pacer cannot "see" an intrinsic wave. By elongating the PVARP, the sensing of a P wave generated in the atrium by feedback is blocked so that PMT is precluded. The teaching of the prior art is to lengthen the PVARP to about 340 ms. The principle disadvantage of this practice is that this lengthening of the PVARP is frequently inadequate. Furthermore, the lengthening of one PVARP for only one period does not preclude recurrence of PMT even if the tendency for it to occur was precluded this once. In addition, this practice does not resolve the case in which a PMT is triggered by a paced pulse or normal intrinsic ventricular wave.

Another attempt to solve the PMT problem is to shorten the atrio-ventricular delay and to set the upper rate or frequency limit at a high level. The resulting enhancement of the likelihood of fatigue is relied upon to stop the PMT. This "cure" appears worse than the "disease".

It has also been proposed that after the PMT is experienced, the physician should elongate the post-ventricular atrial refractory period (PVARP) so that it exceeds the retrograde ventricular-atrial (VA) conduction time. To accomplish this object, the physician programs the pacemaker for a PVARP longer than the anticipated VA conduction time. It is anticipated that the pacemaker then will not respond to the feedback pulse and PMT will be precluded. In some cases, the retrograde VA conduction time is of relatively long duration. Durations as long as 460 to 480 ms have been experienced. It is then necessary, so as to cover all cases, that the pacemaker have the facility to program the PVARP to durations of between 500 and 550 ms and to maintain this function at that duration to suppress or prevent PMT. This alternative, which is put into effect only after the tachycardia is discovered, has the disadvantage that until the patient visits his or her physician, the PMT is not discovered and he or she is subject to the discomfort, distress and hazard of an abnormally rapid heart beat.

Another alternative has been proposed by Intermedics, Inc., P.O. Box 617, 240 Tarpon Inn Village, Freeport, Tex. 77541. the PMT beats occur at precise intervals as compared to sinus tachycardia, the increase in beat rate by reason of exertion. In the practice of the Intermedics method, a predetermined number, typically 15 beats are sampled. If the sampled beats are regular with unchanging intervals between them, PMT is recognized. The Intermedics practice in dealing with PMT, once it is detected, is to block or drop the next ventricular paced beat. The PMT is interrupted. The disadvantage of this method is that it does not prevent the recurrence of PMT.

It is an object of this invention to overcome the above-described drawbacks and disadvantages of the prior art and to provide a method of operating a pacemaker, having leads to both the atrium and ventricle and normally operating in the DDD mode, in whose practice PMT with its discomfort and hazard to the patient shall be automatically detected and automatically suppressed and prevented from recurring before the host visits a physician and in addition, the physican will be made aware of these events.

SUMMARY OF THE INVENTION

In accordance with this invention, a method of operation of a pacemaker is provided in whose practice PMT is detected and on its detection, the pacemaker is set to positively correct for, and eliminate, the PMT automatically and also to signal that PMT has been experienced so that the physician is informed that PMT has occurred and corrective action has been automatically taken. The physician can then reprogram the pacemaker to assure operation free of PMT.

In the practice of the method according to this invention, the PMT is detected by sampling an adequate number, say 15, beats. The post ventricular-atrial refractory period (PVARP) is then automatically lengthened to 500 or 550 ms, or generally to between 500 and 550 ms, and the pacing mode is converted from DDD mode to DDT mode. In addition, the minimum programmed rate of the pacemaker is increased by a small magnitude, typically 5 beats per minute. By the automatic lengthening of the PVARP to the above duration, the discomfort of, and hazard to, the patient is positively eliminated. The "T" in the DDT means triggered. In the DDT mode, the intrinsic P wave in the atrium and the intrinsic QRS wave in the ventricle each elicit a perceptible response from the pacemaker. The intrinsic P wave elicits two responses; namely, a zero delay triggered pulse or spike from the pacemaker to the atrium which is superimposed on, and fuses with, the P wave and a triggered pulse in the ventricle at the end of the AV delay. The AV delay is programmable. In the ventricle in the DDT mode, the triggered response is limited only the ventricle. If a premature ventricular contraction (PVC) occurs, a zero delay pulse is elicited from the pacemaker which is fused with the intrinsic PVC pulse.

Because the PVARP has been lengthened, the upper limit of frequency at which the pacemaker paces is limited. For example, assume that the AV delay is 175 ms and the PVARP is 500. With these parameters, the rate becomes:

$$(60,000)/(175+500)=88 \text{ beats per minute.}$$

This upper limitation is imposed by the necessity of suppressing PMT.

The change in mode to DDT is readily recognized by telephone monitoring or by conventional electrocardiography. The presence of the atrial and ventricular spikes and the presence of a spike on the occurrence of PVC, accompanied by the sinus variation in frequency, indicate that the pacemaker is operating in the DDT mode, that a PMT has occurred and that it has been corrected by permanent adequate lengthening of the PVARP. In this application, the word "spike" is used to distinguish a pacemaker pulse from an intrinsic P or QRS wave. The distinction is based on the difference of appearance between a pacemaker pulse and a P or QRS wave. The spike is readily recognizable. In addition, the automatic lengthening of the PVARP and the conversion to the DDT mode, the minimum rate is increased typically by 5 beats per minute which can also be recognized when the pacemaker operates at the minimum rate. In treating the patient, the physician would leave the pacemaker with the lengthened PVARP or would reduce the PVARP if the patient could accomodate a reduced PVARP. The physician would also reprogram the pacemaker to operate in the DDD mode and would reset the minimum frequency to the originally set magnitude; i.e., he would eliminate the increase of small magnitude (5 beats per minute).

The reason for adding the typical 5 beats per minute will now be explained. Assume that the pacemaker is programmed to a minimum frequency of 60 beats per minute and that the patient has developed PMT so that the PVARP has automatically been lengthened. If, during the monitoring when producing an ECG, the patient's heart beat is at the minimum rate, it might not be possible for the physician to recognize that PMT had occurred. The monitor or the ECG would show that the atrium and ventricle are being paced in sequence at the minimum rate, 60 beats per minute, and spikes would appear as the paced pulses. The increase from 60 to 65 beats per minute can readily be recognized on the monitor or the ECG. With the heart-beat frequency increased to 65 beats per minute in accordance with this invention, the physician can readily recognize that the frequency has been increased because PMT has occurred and has been corrected.

BRIEF DESCRIPTION OF THE DRAWINGS

For a better understanding of this invention, both as to its organization and as to its operation, together with additional objects and advantages thereof, reference is made to the following description taken in connection with the accompanying drawings, in which:

FIG. 14 is a pacing ladder diagram for aiding in the understanding of FIG. 7, lines A, B, C.

DETAILED DESCRIPTION OF PRACTICE OF THIS INVENTION

Figure 1:
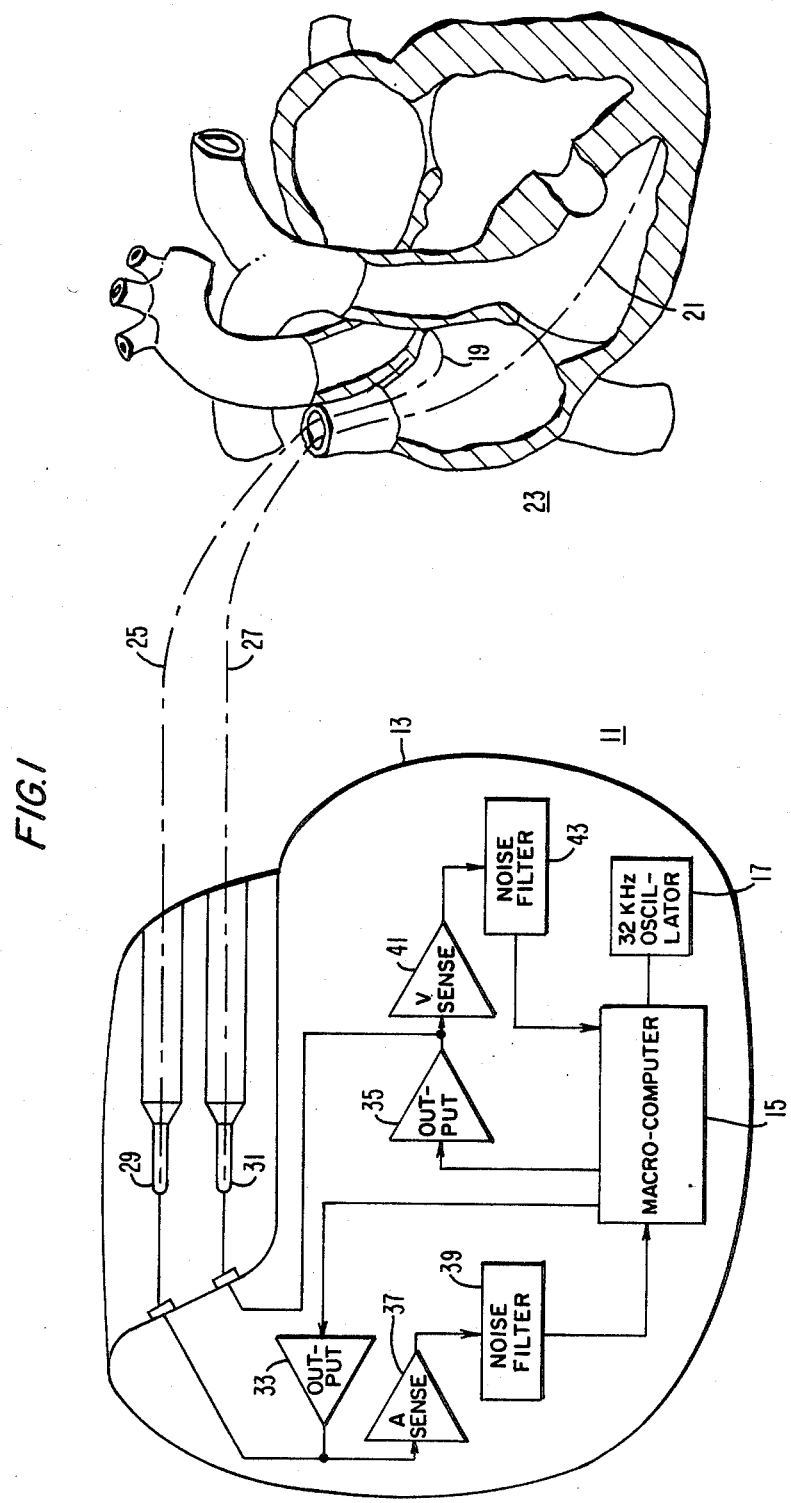
FIG. 1 is a block diagram of a typical implanted pacemaker unit used in the practice of this invention.

FIG. 1 shows a pacemaker 11 having a casing 13 whose dimensions permit the pacemaker to be implanted in a host without discomfort. Within the casing 13 where is a micro-computer 15 provided with an adequate memory to command the carrying out of the functions of the pacemaker and an adequate power supply (not shown). The computer 15 is driven by an oscillator 17 which serve as a clock for the computer. The atrium 19 and the ventricle 21 of the heart 23 of the host in whom the pacemaker is implanted are stimulated through atrial and ventricular leads 25 and 27 respectfully connected to the output terminals 29 and 31 of the pacemaker. Pulses are supplied to the atrial lead 25 via terminal 29 through output amplifier 33 which is enabled or disabled at the commands of the computer 15. Pulses are supplied to the ventricular lead 27 via terminal 31 through amplifier 35 which is likewise enabled and disabled by the computer. The atrium is sensed for intrinsic P waves and other phenomena through lead 25, terminal 29 and amplifier 37. Amplifier 37 transmits the intelligence which it receives to the computer 15 via noise filter 39. The ventricle is sensed for intrinsic QRS waves and the pulses resulting from premature ventricular contraction and other phenomena through lead 27, terminal 31 and amplifier 41. Amplifier 41 transmits the intelligence which it receives to computer 15 through filter 43. The computer 15 can be programmed to command the pacemaker to perform its functions by a counter which transmits the appropriate number of magnetic pulses to program the computer for the desired operation.

Figure 2A:
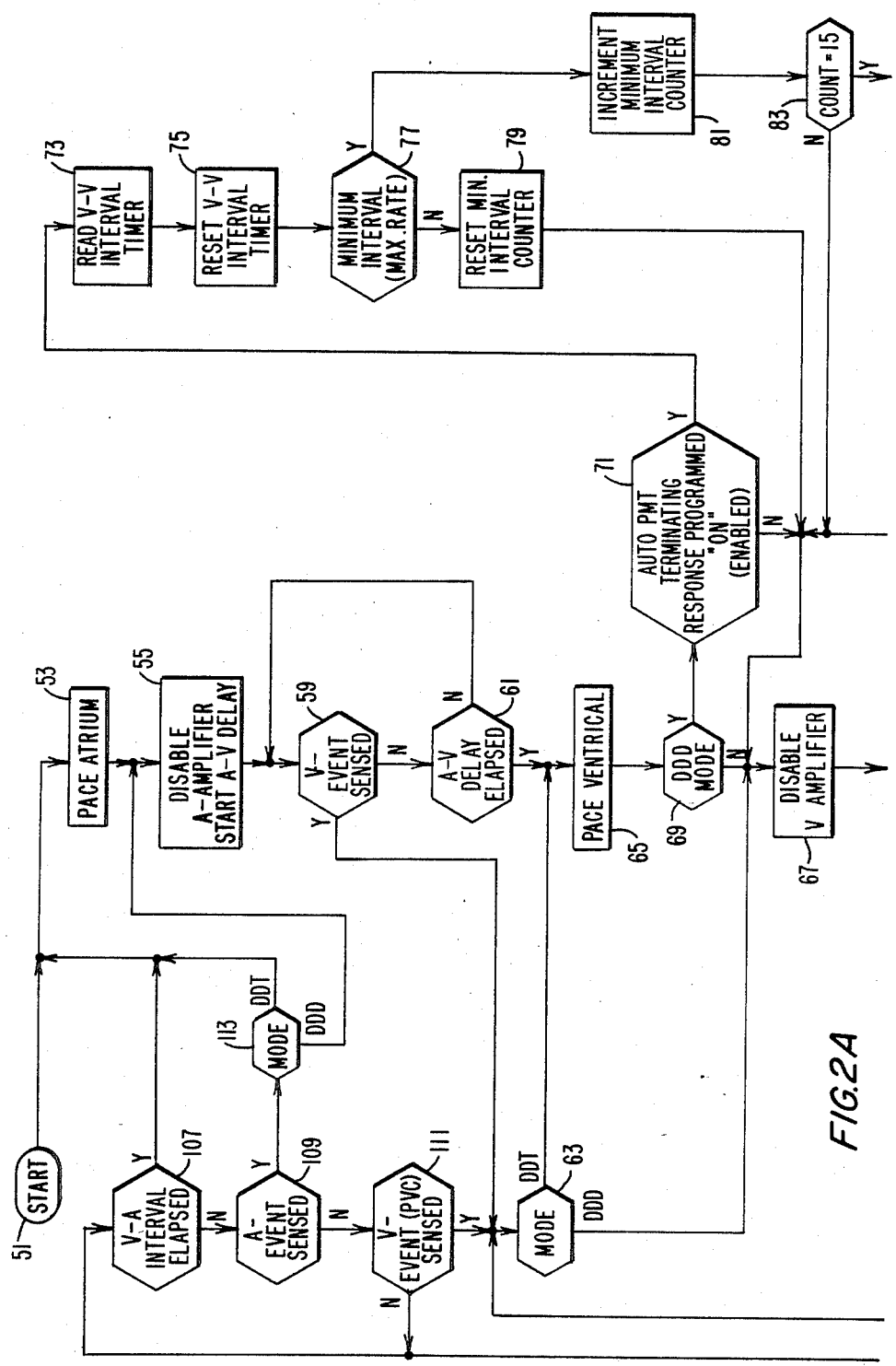
FIGS. 2A and 2B together constitute an algorithm for programming the pacemaker shown in FIG. 1 to practice this invention.
Figure 2B:
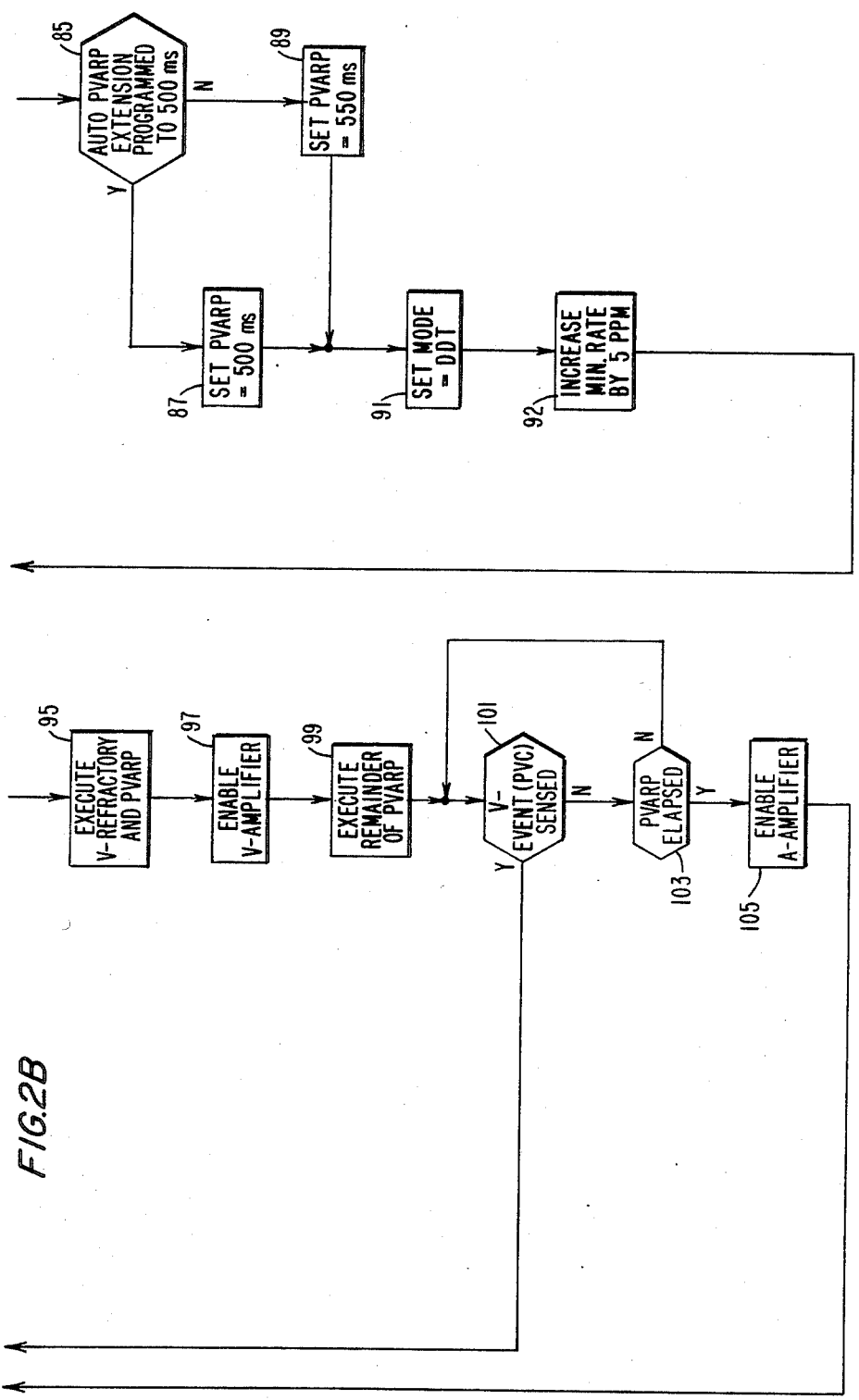

With reference to FIGS. 2A and 2B, the start block 51 may be regarded as the start of an operation at any time, arbitrarily chosen as a point of reference, when the pacemaker is in use in the host. It is assumed that the start is with an atrial event. A dual chamber pacing cycle can begin with any cardiac event whether paced or spontaneous. The block 53 indicates that, at the instant selected, a pulse or spike from the pacemaker 11 is transmitted to the atrium 19 through amplifier 33. It is assumed that the pacemaker 11 is set in the DDD mode when the pacing cycle is started. As indicated in block 55, the A-amplifier 37 is disabled so that it does not sense the atrial pulse transmitted. In addition, AV delay is started to time out. During this delay, the atrial amplifier 37 is disabled. During the AV delay, the ventricular sensing amplifier 41 is polled repeatedly to determine if there had been a ventricular event. This sensing is indicated by decision block 59. So long as the answer in decision block 61 is "No"; i.e., that the AV delay has not expired, the sensing of V through V-amplifier 41 continues. This sensing is for the purpose of determining if there has been an intrinsic ventricular wave.

Now, assume that a ventricular event (a QRS wave) has been sensed during the AV delay; i.e., the answer in block 59 is "Yes". The algorithm then determines whether the pacemaker 11 is in the DDT mode or in the DDD mode as indicated in decision block 63. If the pacemaker is in the DDT mode, the ventricle is paced as indicated in block 65; i.e., a spike is produced with zero delay, and the pacing cycle is continued as indicated by the sequence 66 of vertical arrows in the algorithm. If block 63 indicates that the mode is DDD, the V-amplifier 35 is disabled as indicated by block 67 and the pacing cycle continues from this point as indicated by the verticle arrows 66.

Now, assume that no ventricle event has been sensed; i.e., the answer in decision block 59 remains at "No" until the answer to block 61 becomes "Yes". The ventricle 21 is now paced, as indicated by block 65 and the pacemaker is polled to determine if it is in the DDD mode as indicated by block 69. If the answer is "No", the pacemaker 11 continues to operate as indicated in sequence 66 by the vertical arrows. This operation is in the DDT mode.

Now, assume that the answer of decision block 69 is "Yes" i.e., the pacemaker is in the DDD mode. A decision is now sought, as indicated by block 71, whether the automatic PMT-terminating response has been programmed to "ON". If the PMT-terminating response is not "ON", the pacemaker continues to carry out the pacing cycle in the DDD mode as commanded by sequence 66.

Now, assume that the answer of decision block 71 is "Yes"; i.e., the PMT-terminating response has been programmed to "ON". The duration of the most recent V—V interval (interval between ventricular events) is evaluated to determine if a PMT exists by reading a V—V timer in the computer 15 as indicated in block 73. The timer measures the interval between ventricular events. After each measurement, the timer is then reset as indicated by block 75 so that it can measure the next V—V interval. The V—V interval is then evaluated, as indicated by block 77, to determine if the read (most recent) interval was equal to the minimum possible V—V interval; i.e., the interval which gives rise to a PMT. If the evaluated interval is not equal to the minimum interval, the minimum interval counter, which is a register, is reset as indicated by block 79. The pacemaker then follows the normal operation in the sequence 66.

Now, assume that the evaluation reveals that the V—V interval is the minimum interval. The minimum-interval counter is now incremented, as indicated by block 81, instead of being reset and the counter is checked as indicated by decision block 83 to determine if there has occurred 15 (or any other specified number) of successive minimum intervals. If the answer is "No", the pacemaker continues to cooperate in accordance with the sequence 66.

Assume that the count is 15. A determination is now made, as indicated by block 85, as to how the physician has programmed the computer 15 for PVARP. If the computer has been programmed to PVARP=500 ms, the PVARP is set at this magnitude as indicated by block 87. If the answer of block 85 is "No", the PVARP is set at 550 ms as indicated by block 89. The mode of the pacemaker 11 is now programmed to DDT as indicated by block 91 and the minimum pacing rate of the pacemaker is increased by 5 pulses per minute as indicated by block 92.

The V-A interval is now started by disabling the V-sensing amplifier 41 as indicated by block 67 in sequence 66 and timing the ventricle refractory period and PVARP as indicated by block 95. Since the duration of PVARP is equal to or longer than the duration of the ventricular refractory period, the timing of this period and the timing of PVARP are started simultaneously. After the ventricular refractory period times out, the V-sensing amplifier 41 is enabled, as indicated by block 97, so that any ventricular event which occurs can be sensed. The remainder of PVARP then times out as indicated by block 99. During the remainder of PVARP, the ventricular sensing amplifier 41 is repeatedly polled for a ventricular event, a PVC, as indicated by decision block 101. If a ventricular event has not occurred on any check (a "No" from block 101) a determination is made if PVARP has timed out as indicated by block 103. If PVARP has not elapsed, the pacemaker is checked anew for a ventricular event.

If a ventricular event is sensed during PVARP, a check is made to determine the pacing mode as indicated by block 63. If this mode is DDT, the ventricle 21 is paced producing a spike on the ventricular pulse which was sensed. The PVARP is reset and the sequence 66 is carried out. If the mode is DDD, the V-amplifier 41 is disabled (block 67) and the sequence 66 is carried out.

Now, assume that no ventricular event (PVC) has been sensed during PVARP. When PVARP expires, sensing A-ampifier 37 is enabled as indicated by block 105. The V-A interval will then be checked repeatedly, as indicated by block 107, to determine if it has timed out. If the answer is "No", the V-A interval has not timed out, the A-sensing amplifier 37 is checked for an atrial event as indicated by block 109. If not atrial event has occurred, the ventricular sensing amplifier 41 is checked to determine if a ventricular event, a PVC, has occurred as indicated by block 111. If no ventricular event has occurred, the just described cycle involving decision blocks 107, 109, 111 is repeated. If the V-A interval expires without any atrial or ventricular event, "Yes" for block 107, the atrium is paced as indicated by block 53 so that the whole cycle is repeated.

Now, assume that an atrial event has occurred; i.e., an intrinsic P wave has been sensed. The pacemaker 11 is checked for mode, as indicated by decision block 113. If the pacemaker is in DDT mode, an atrial spike is superimposed on the intrinsic P pulse. If the mode is DDD, the atrium 19 is not paced. Instead the A-amplifier is disabled, as indicated by block 55, and the normal pacing cycle, sequence 66, is repeated.

If a ventricular event; i.e., a PVC, is sensed, the pacing mode is checked as indicated by block 63. If the pacemaker is in the DDT mode, the ventricle 21 is paced to produce a spike, as indicated by block 65, and the normal pacing cycle, sequence 66, continued from this point. If the pacemaker 11 is in the DDD mode, the V-amplifier 41 is disabled, as indicated by block 67, and the normal cycle continued from this point.

At the time of pacemaker implant or at any time thereafter, the automatic PM-terminating response (block 71) can be programmed to either the "ON" (enabled) or "OFF" (disabled) condition. Also, the automatic extension of the PVARP interval (in response to a PMT) can be programmed for either 500 or 550 ms, with 550 ms being recommended for maximum effect.

From the above description, it can be understood that until a PMT condition is detected, the pacemaker operates in the DDD mode. That is, both chambers 19 and 21 of the heart 23 are paced and both chambers of the heart are sensed for spontaneous cardiac events. If a P wave (atrial event) is sensed in the DDD mode, the pacemaker responds by inhibiting its atrial output pulse and by initiating (triggering) and A-V delay period. At the end of the A-V delay period, assuming no spontaneous events were sensed in the ventricle, the pacemaker will generate an output pulse to the ventricle 21. If an R wave (ventricular event) is sensed during the A-V delay, the pacemaker responds by inhibiting its ventricular output pulse and then timing the V-A interval, commencing with the ventricular refractory period and PVARP. Likewise, if a PVC is sensed, the pacemaker responds by inhibiting its ventricular output pulse and then timing the V-A interval, commencing with the ventricular refractory period and PVARP.

If the automatic PMT-terminating response had previously been programmed to the "OFF" (disabled) condition, any subsequent PMT condition that occurs will not be terminated by the pacemaker. Nor will the pacemaker alter the PVARP period or the operating mode in order to indicate that the PMT occurred. Instead, the pacemaker will continue to operate in the DDD mode, thereby sustaining the PMT indefinitely.

If the automatic PMT-terminating response had previously been programmed to the "ON" (enabled) condition, the PVARP is programmed automatically either to 500 or 550 ms duration (depending upon which one had previously been programmed) both to terminate the existing PMT and to prevent the recurrence of future PMT's when a PMT condition is now detected and qualified. Then the minimum programmed rate is automatically increased by five (5) pulses per minute and the mode of operation is automatically changed from DDD to DDT indicating to a physician or a pacer monitoring service that a PMT occurred and has been corrected. These changes to the PVARP, the operating mode and the minimum rate are latched in such a way that they cannot be further altered by the pacemaker itself. Only by means of external reprogramming by a physican can the operating mode and parameters be further changed.

In the DDT mode, the pacemaker exhibits a triggered response to any sensed cardiac events. Thus, when a P wave is sensed, the pacemaker will immediately generate an output pulse to the atrium so that a spike will appear in the P wave. This impulse will not depolarize the atrium (since depolarization has already been initiated) but will simply fuse with the P wave. At the same time, in response to the sensed P wave, the pacemaker will initiate the A-V delay period, after which an output pulse would be generated to the ventricle. Thus, in the DDT mode, the pacemaker responds to an intrinsic P wave in a dual fashion: one is a triggered response to the atrium and the other is a delayed triggered response to the ventricle.

Similarly, while in the DDT mode, the pacemaker exhibits a triggered response to QRS waves sensed in the ventricle. However, unlike the triggered response to events sensed in the atrium, the triggered response to events sensed in the ventricle is limited to the ventricle only. If an intrinsic event such as a PVC is sensed in the ventricle while the pacemaker is functioning in the DDT mode, the pacemaker 11 will immediately generate an output pulse to the ventricle. This will produce a spike in the QRS wave which will fuse with the already-initiated depolarization thereby causing no competition. (In contrast, while functioning in the DDD mode, the pacemaker responds to a PVC by inhibiting the generation of an output pulse to the ventricle.)

Pacemakers with which this invention is practiced are typically delivered with the automatic PMT-terminating response programmed to the "ON" (enabled) condition and the automatic extension of the PVARP interval programmed to 550 ms.

In all graphs or ECG's of FIGS. 3 through 14, time is plotted horizontally and amplitude vertically. FIGS. 3A, B, C, D are based on operation of pacemaker 11 in the DDD mode. For the explanatory purpose which FIGS. 3A, B, C, D serve, it is assumed that each common vertical line through all four graphs intersects the abscissa of each graph at a point measuring the same instant of time. FIG. 3A presents the graph or ECG for the situation in which both the atrium and the ventricle are paced. The pacing period is 800 ms as shown. A spike 121 is impressed on the atrium 10 (FIG. 1) and after the A-V delay (160 ms), a spike 123 is impressed on the ventricle 21 (FIG. 1). The spike 121 stimulates an atrial wave 125 similar to a P wave, and the spike 123 stimulates a ventricular wave 127 similar to a QRS wave. The stimulated wave 125 follows the impressed spike 121 and the stimulated ventricular wave 127 follows the impressed spike 123.

FIG. 3B presents the situation where the atrial pulse is an intrinsic P wave 129 and the pacer spike 121 is suppressed. The intrinsic atrial wave 129 occurs earlier than the pulse stimulated by spike 121. The pacemaker senses the wave 129 and produces the spike 123 after the A-V delay. The spike 123 and the stimulated wave 127a occur earlier than the corresponding spike 123 and wave 127 in FIG. 3A. FIG. 3C presents the graph or ECG for the situation where the atrial event is an intrinsic P wave 129 and the ventricle event is an intrinsic QRS wave. FIG. 3D presents the graph for the situation where the ventricular event is an intrinsic wave 131.

Figure 3:
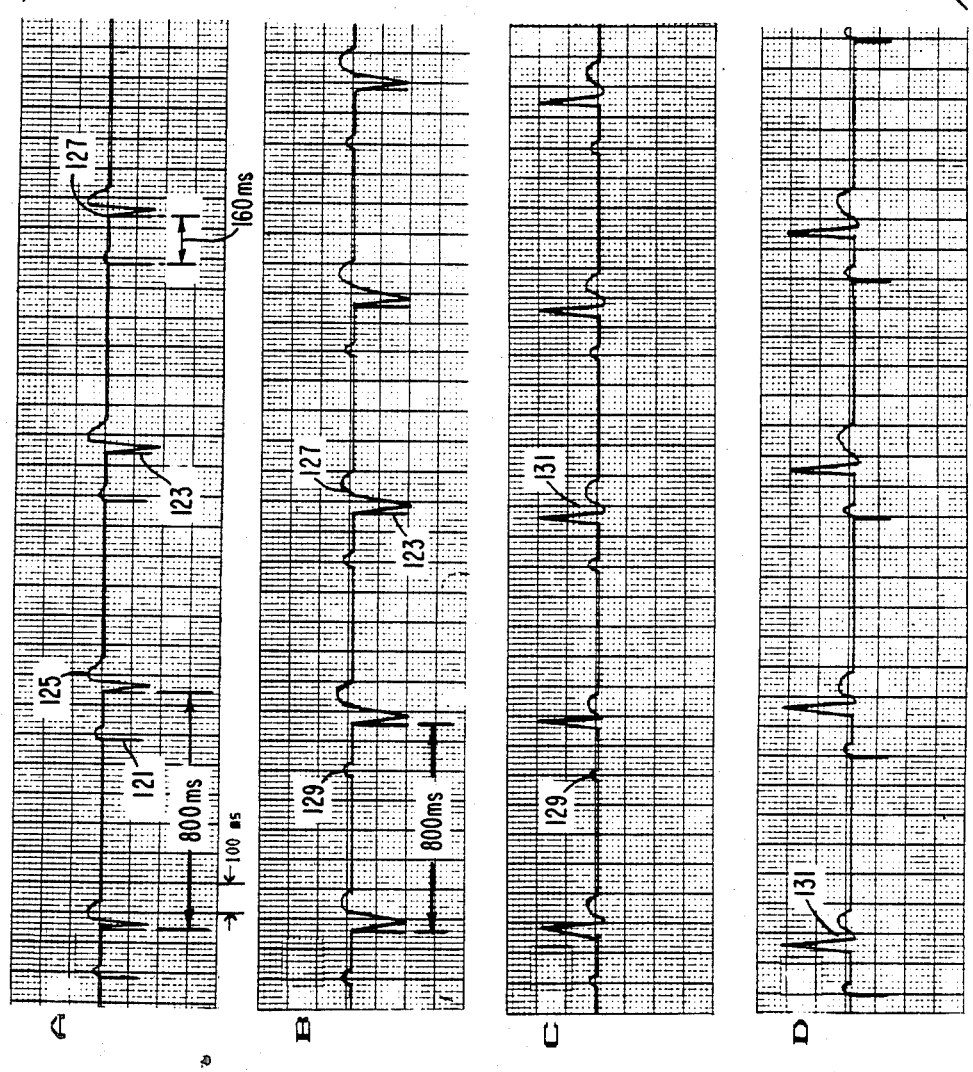
FIG. 3 lines A, B, C, D is a graph simulating an ECG for normal operation of a pacemaker.
Figure 4:
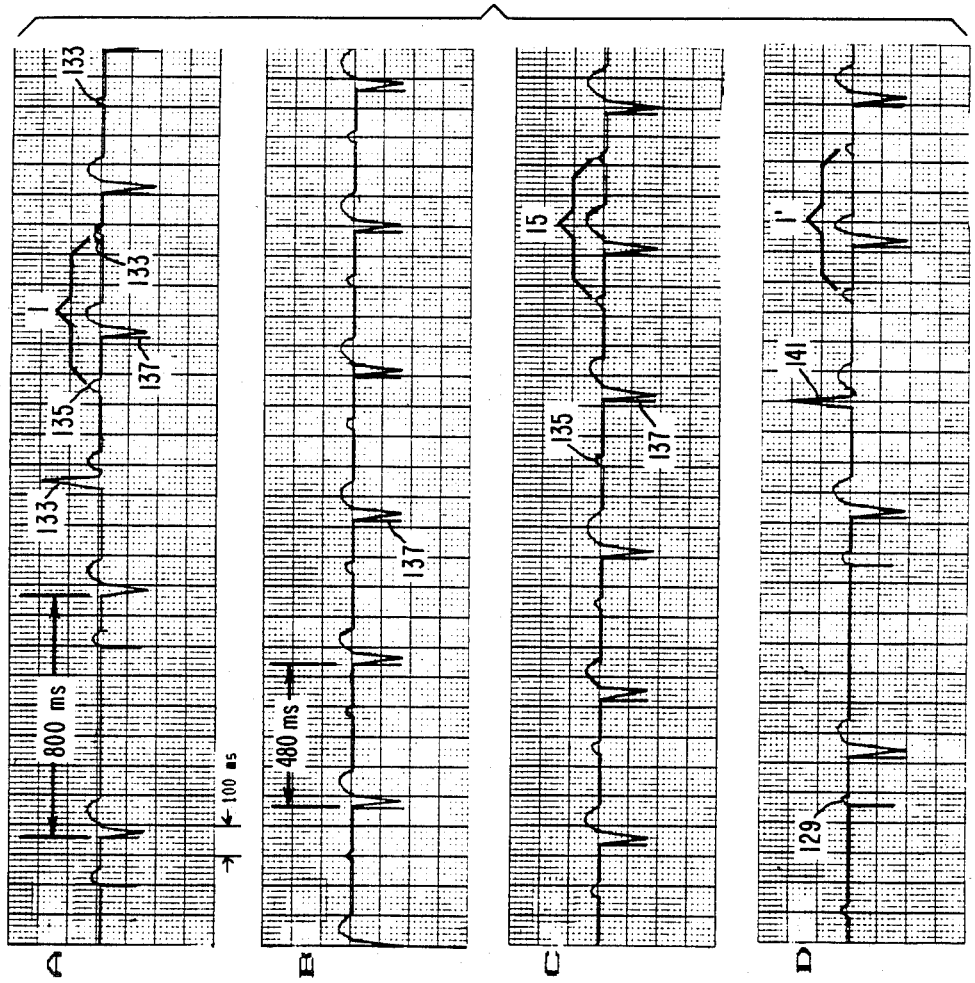
FIG. 4, lines A, B, C, D is a graph similar to FIG. 3 showing the occurrence of tachycardia stimulated by a PVC; and its termination by the prior art by dropping the pacer output to the ventricle on the sixteenth beat.

FIGS. 4A, 4B, 4C and 4D are based on the operation of pacemaker 11 in the DDD mode. These views present a continuous graph in which the graphs or ECG's in 4B, 4C, 4D follow 4A in succession. FIG. 4A shows the occurrence of an intrinsic retrograde PVC wave 133. This stimulates an intrinsic atrial P wave 135. The pacemaker senses the wave 135 producing a ventricular pulse 137 after A-V delay. This pulse 137 stimulates another retrograde atrial P wave 138 and the operation is repeated generating a PMT condition with the period between events, typically 480 ms or a beat frequency of 125 beats per minute. Each ventricle pulse 137 stimulates a QRS wave which is labeled 139 to distinguish this wave from the QRS wave 131 produced during normal operation (FIG. 3). The first PMT cycle is labeled "1" in FIG. 4A and the 15th is labeled 15. During the following (16th) cycle the ventricular output is inhibited, in accordance with the teachings of the prior art, as indicated by the absence of a pacemaker pulse and a stimulated QRS wave near the beginning of FIG. 4D. The remainder of FIG. 4D shows the disadvantage of this prior-art approach. After one normal cycle—in actual practice there may be several—there is a new retrograde PVC wave 141 and a new PMT is again generated. The first cycle of the PMT is labeled 1.

Figure 5:
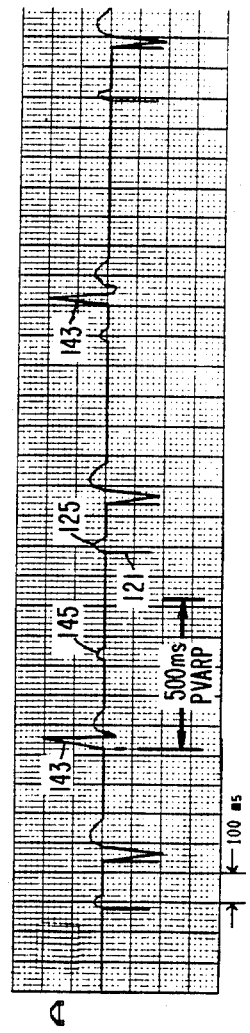
FIG. 5 is a graph similar to FIG. 3 illustrating temporary prevention of tachycardia in accordance with the teaching of the prior art.
Figure 6:
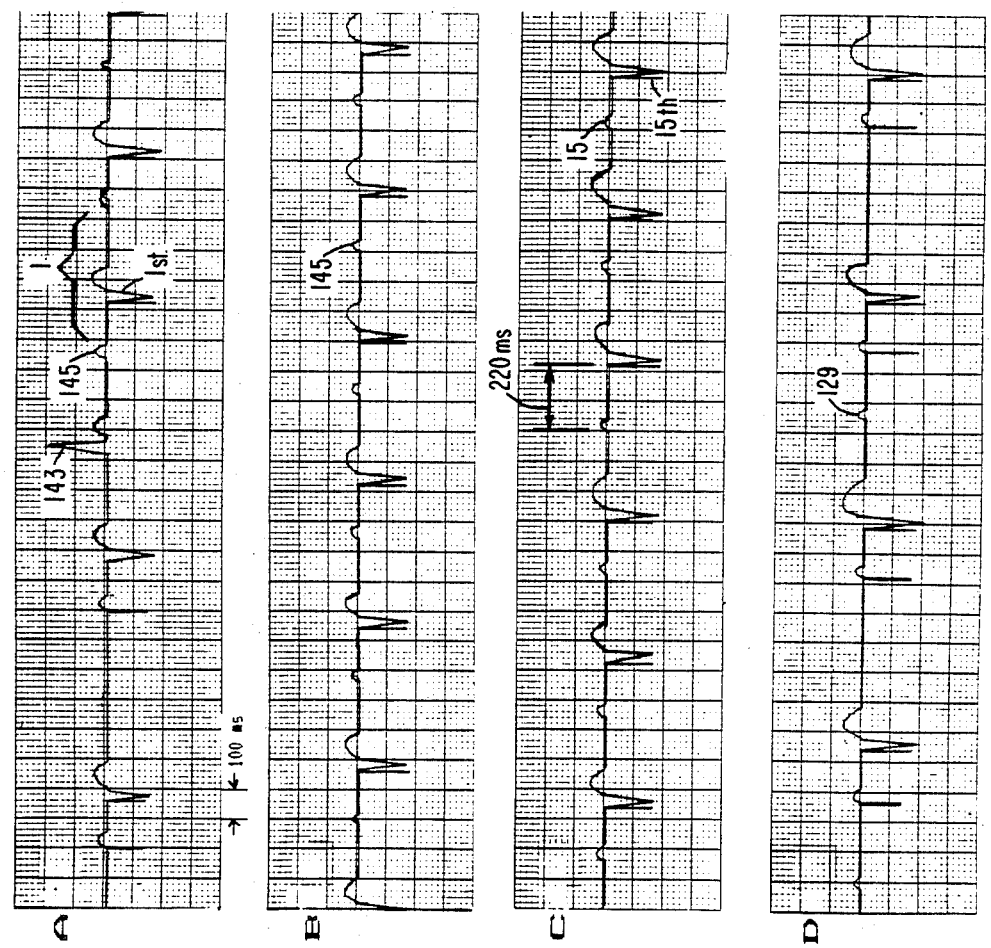
FIG. 6, lines A, B, C, D is a graph similar to FIG. 3 showing interaction of the heart of the host and an implanted pacemaker in the practice of this invention.

FIG. 5 is also based on a pacemaker operating in the DDD mode. This view presents prior-art operation. On the occurrence of a retrograde PVC, 143, the PVARP is elongated precluding a PMT. The elongation starts with the PVC and has a duration such that the total PVARP is 340 ms. The pacemaker 11 does not sense the intrinsic P wave 145 during the PVARP so that there is no paced ventricular pulse. The next event is a paced atrial pulse 121 followed by a stimulated atrail wave 125. The disadvantage in this case is that the retrograde PVC reoccurs requiring renewed elongated of PVARP so that the heart beat of the host may be irregular. In addition, this prior-art approach does not provide protection against PMT generated by other phenomena than the PVC. Further, the 340 ms is not of long enough duration to assure that the tachycardia will not persist.

FIGS. 6A, B, C, D discloses an aspect of the invention. The pacemaker operates in the DDD mode. Following the occurrence of a PVC (143 FIG. 6A), fifteen PMT cycles are counted. After the 15th count, the PVARP is automatically elongated to 550 ms. The sensing of the 16th QRS wave is suppressed so that no paced ventricular event is produced at this point or later. The pacemaker then operates normally with the elongated PVARP.

Figure 7:
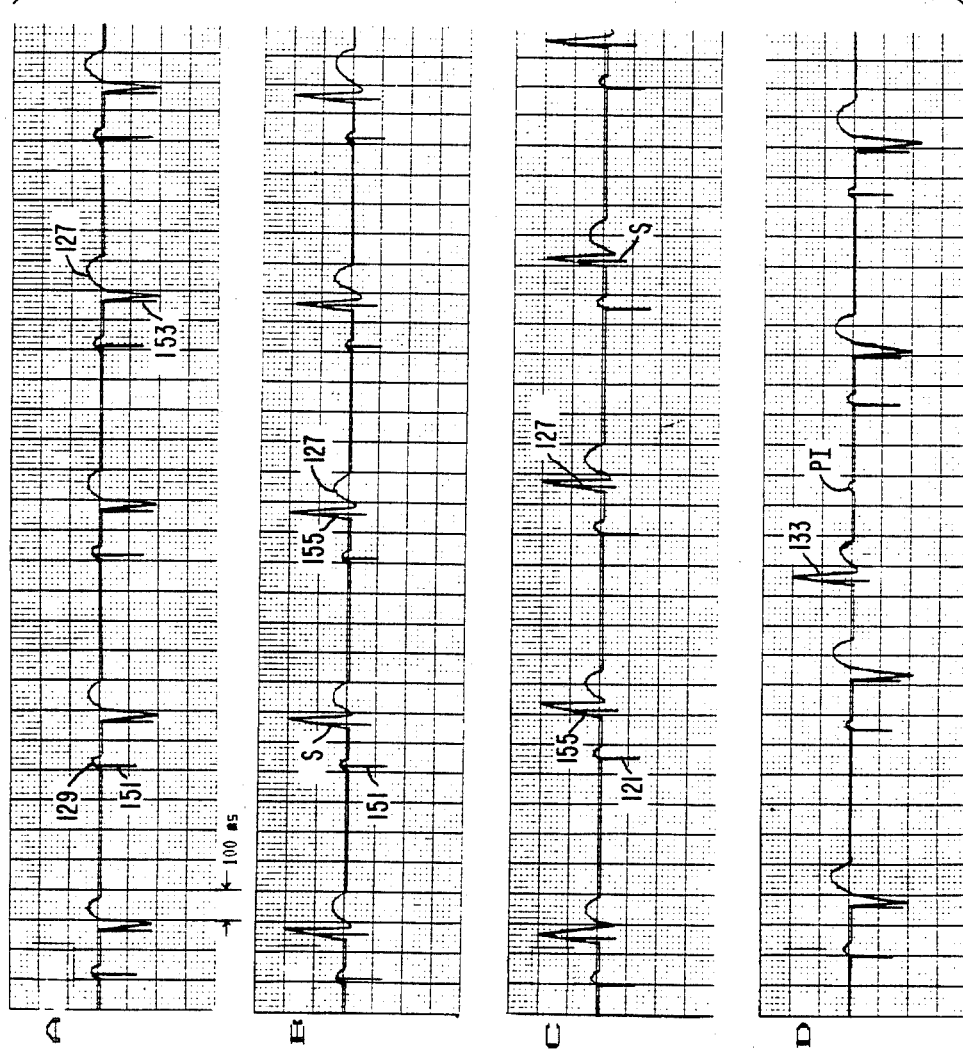
FIGS. 7A, B, C, D is a graph similar to FIG. 3 showing interaction of the host with an implanted pacemaker operating in the DDT mode in the practice of this invention.
Figure 8:
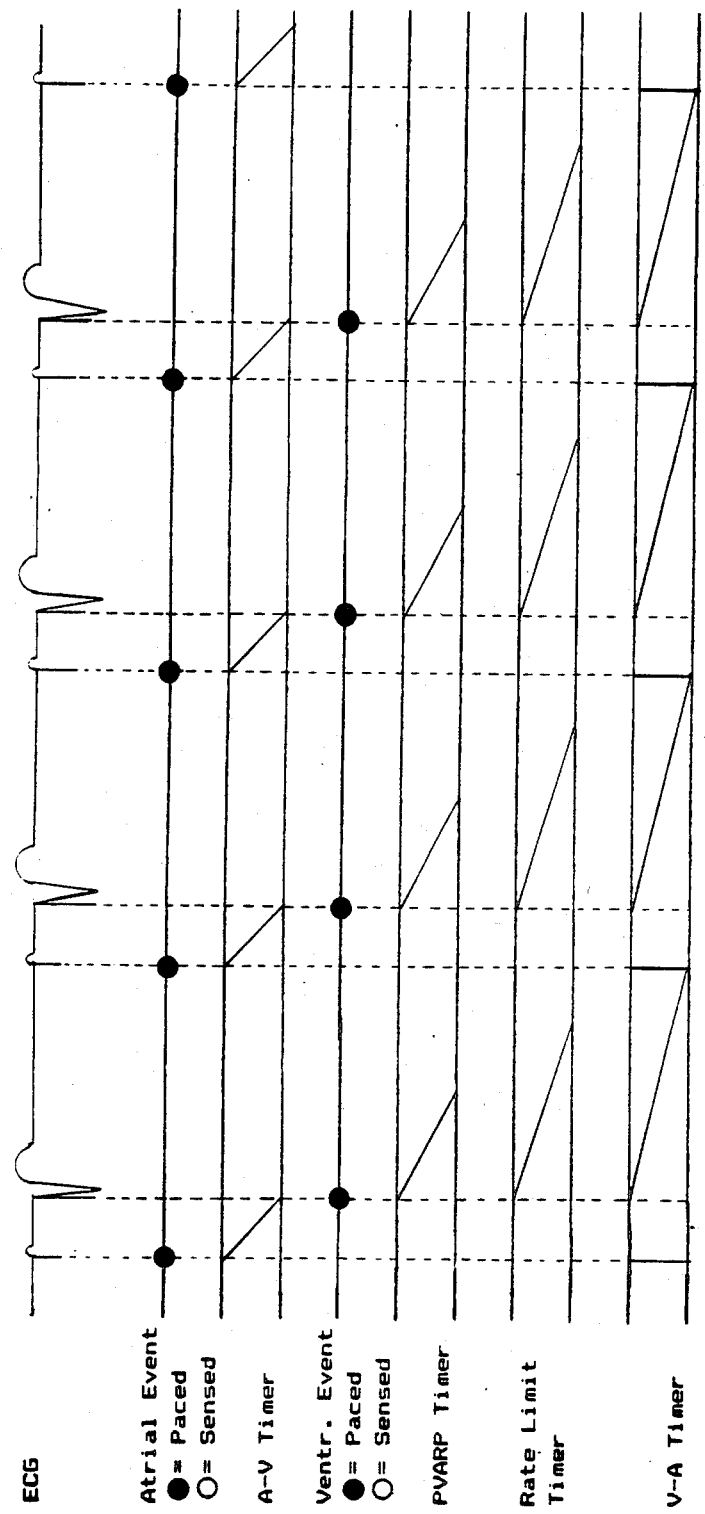
FIGS. 8 and 9 are pacing ladder diagrams for aiding the understanding of FIG. 3.
Figure 9:
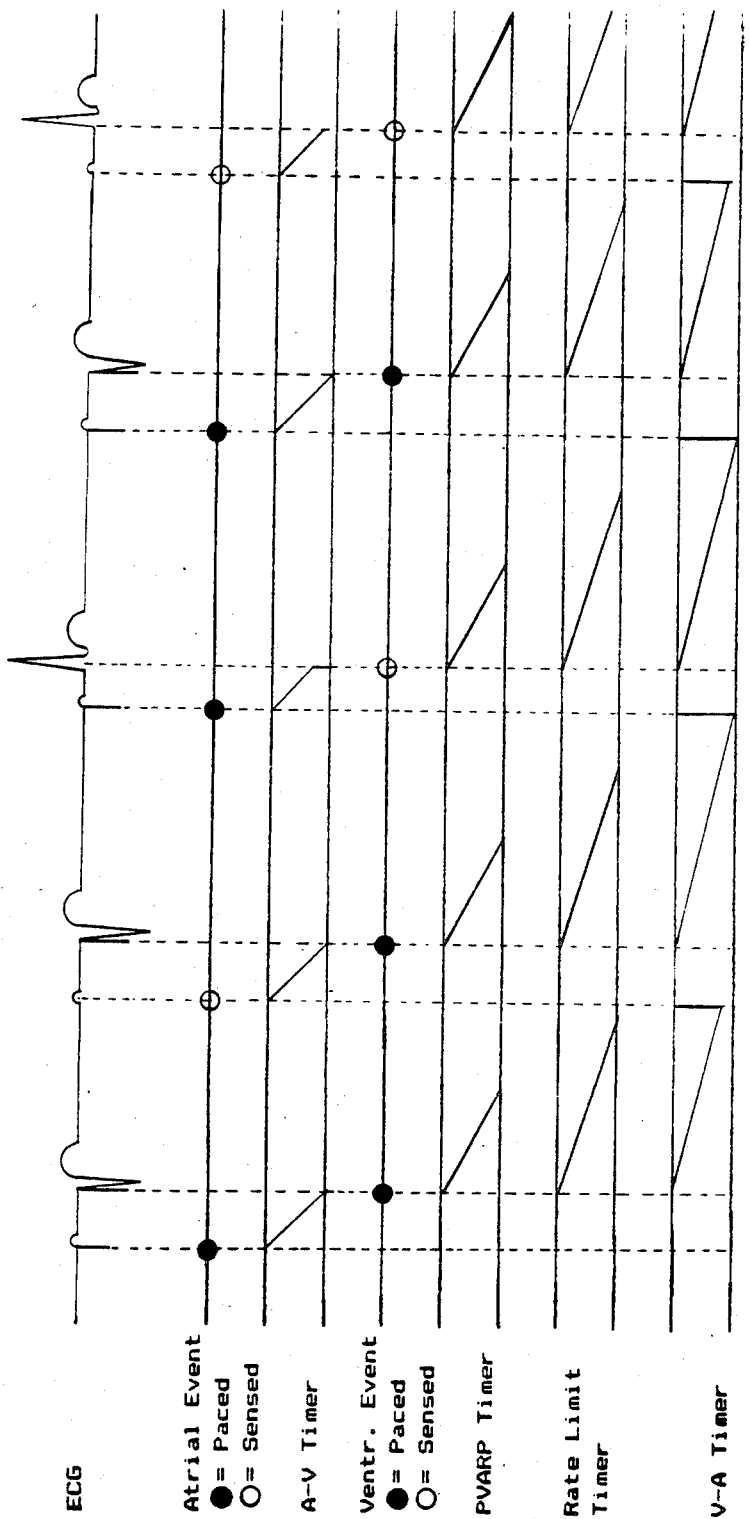
Figure 10:
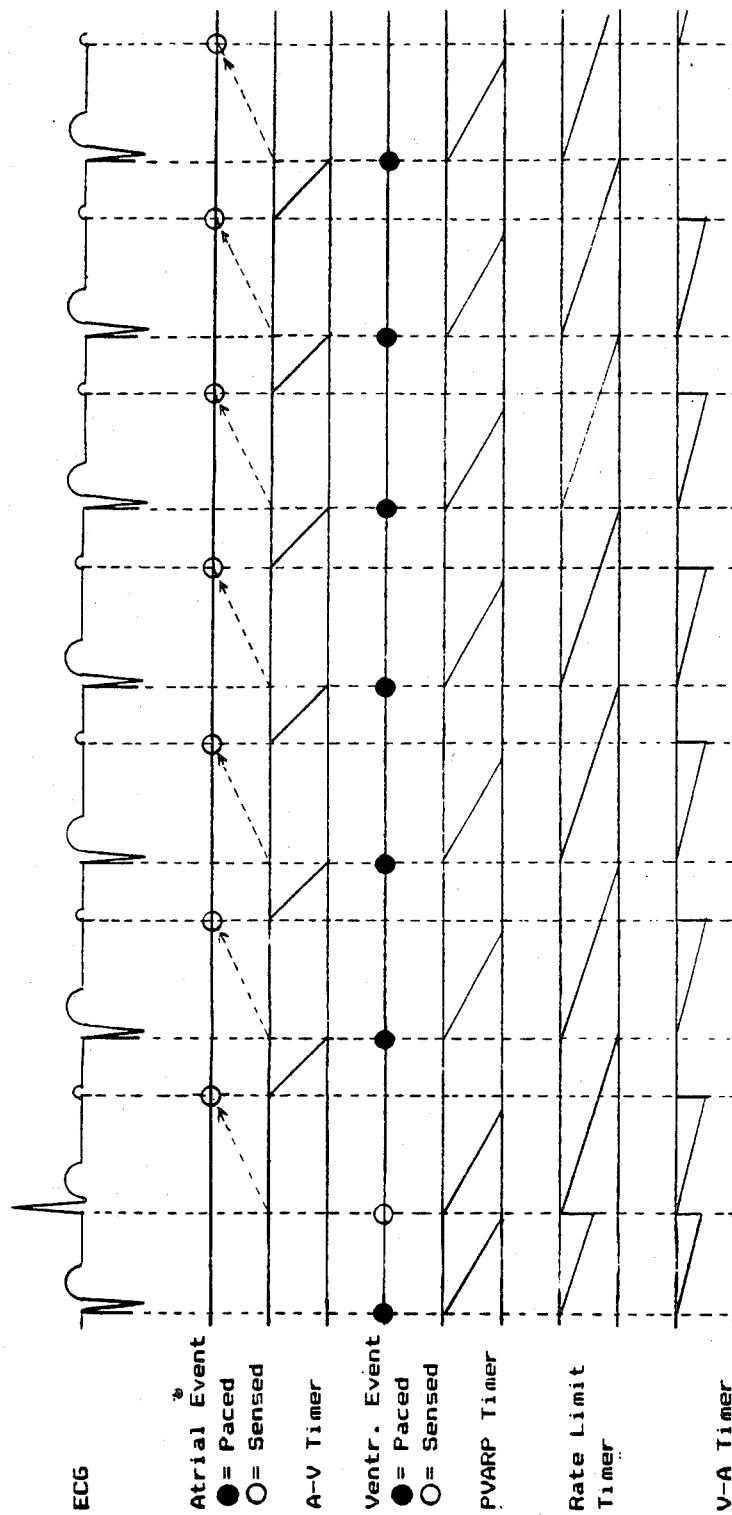
FIG. 10 is a pacing ladder diagram for aiding in the understanding of FIG. 4 and FIG. 6, lines A, B, C.
Figure 11:
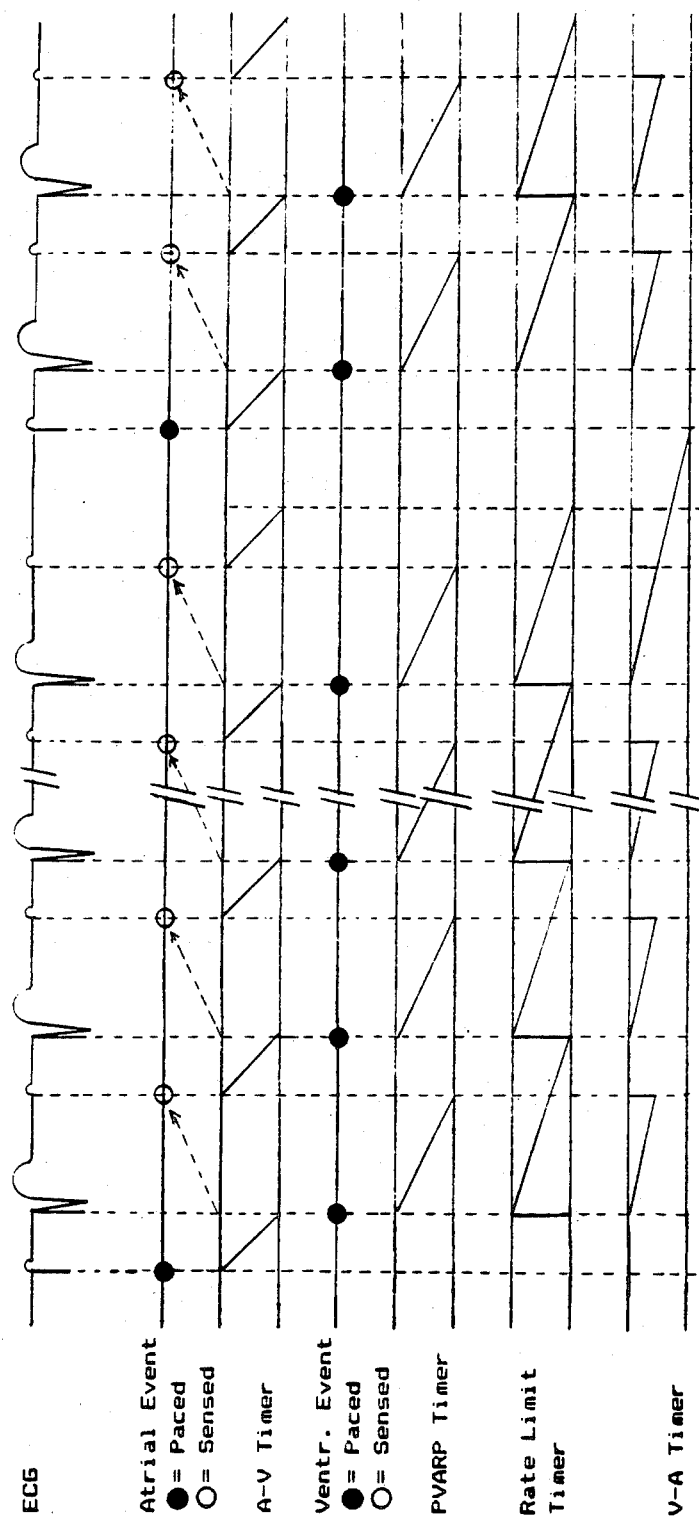
FIG. 11 is a pacing ladder diagram illustrating the prior art practice of dealing with a PMT.
Figure 12:
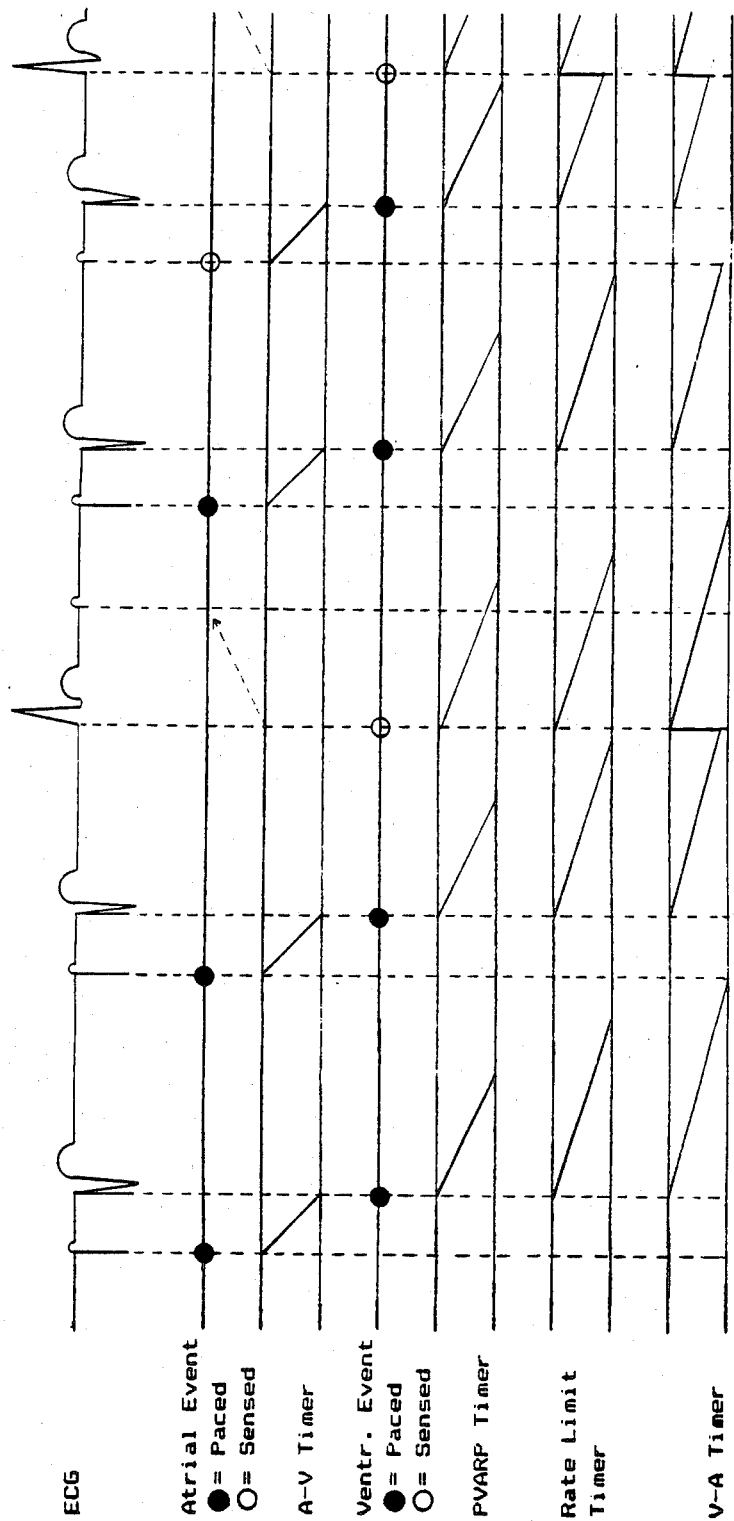
FIG. 12 is a pacing ladder diagram for aiding in the understanding of FIG. 5.
Figure 13:
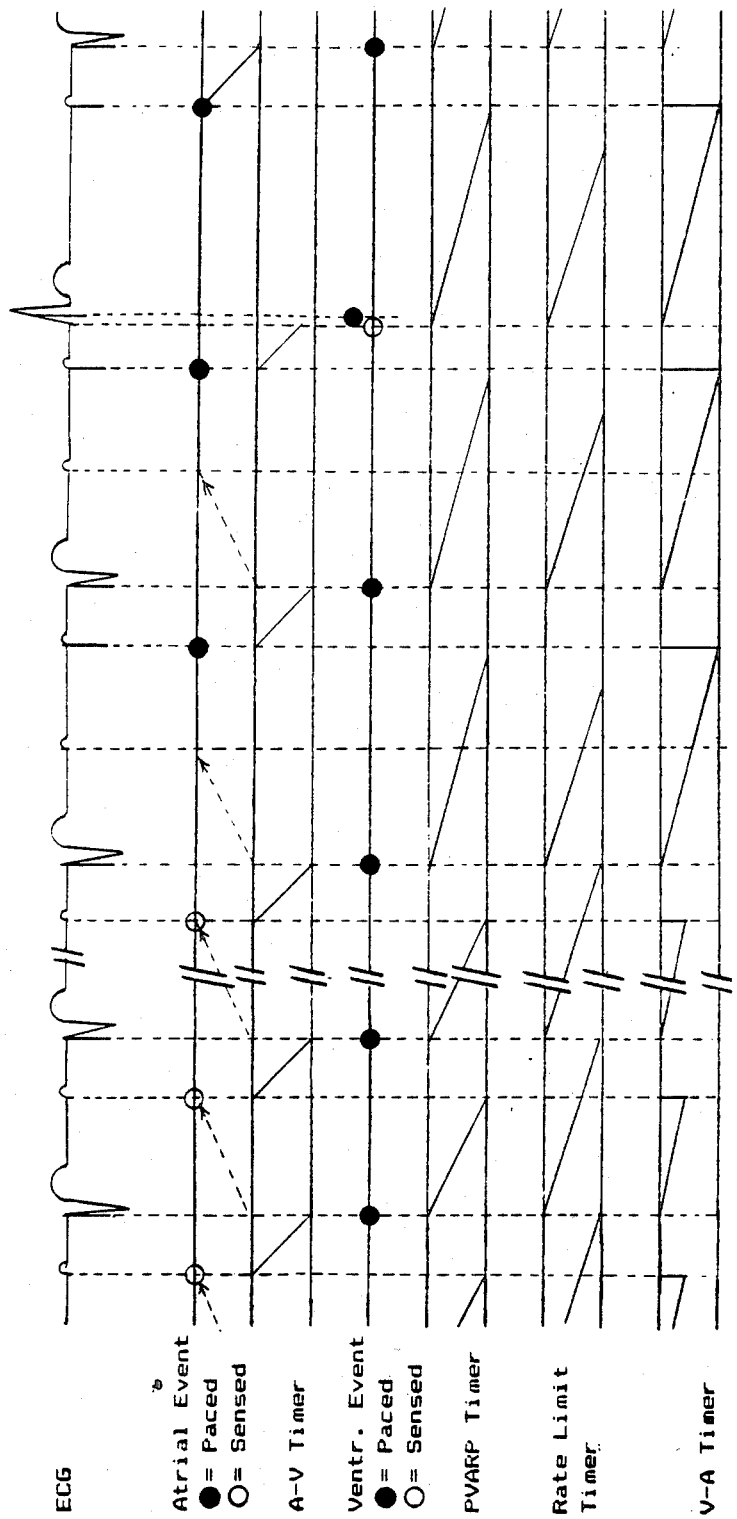
FIG. 13 is a pacing ladder diagram for aiding in the understanding of FIG. 6, line D and FIG. 7C.

FIG. 7 shows the practice of this invention with the pacemaker operating in the DDT mode. FIG. 7A shows the situation in which there are intrinsic P waves while the ventricle is paced. A spike 151 is superimposed on the P wave 129. PMT is precluded by elongation of PVARP. The spike 151 is impressed slighlty after the start of the P wave as shown in FIGS. 1A and 1B. In the case of the ventricular event, the paced pulse (spike) 153 is at the start of the stimulated QRS wave 127. That a PMT has occurred and been suppressed and that the pacemaker is operating in PMT mode is indicated by the delayed spike 151 on each intrinsic P wave 129. FIG. 7B presents the situation in which both the atrial event and the ventricular event are intrinsic. In this case, spikes 151 and 155 are impressed both on the P wave 129 and on the QRS wave 127. In both cases, the spike 151 or 155 is delayed from the start of the wave. That a PMT has occurred and been suppressed and that the pacemaker is operating in PMT mode is indicated by the delayed spike in each intrinsic P wave and QRS wave. FIG. 7 C presents the situation in which the atrium 19 is paced and the ventricular event is intrinsic. FIG. 7D shows the occurrence of a retrograde PVC, 133. Any ventricular event automatically resets the PVARP. In this case, the PVARP would be reset and start timing out on the occurrence of PVC 133. A PMT is precluded.

FIGS. 8 through 14 require no extended explanation in view of their labeling. In the ECG at the top of each view, time is plotted horizontally and amplitude vertically. The points of intersection of any vertical line with the horizontal lines in each graph, for example, the points of intersection of the broken vertical lines and the solid horizontal lines, measures the same respective instants of time. The sloping solid lines represent timing out of an interval from the upper horizontal line to the lower horizontal line.

While preferred practice of this invention has been disclosed herein, many modifications thereof are feasible. This invention is not to be restricted except insofar as is necessitated by the spirit of the prior art.

We claim:

1. The method of operating a cardiac pacemaker while said pacemaker is in a host, said pacemaker having leads connected to the atrium and to the ventricle and having means for controlling the supply of pulses through said leads to said atrium and ventricle, said method being practiced while said pacemaker is in use in said host and comprising: normally operating said pacemaker in the DDD mode, automatically monitoring the operation of said pacemaker for the occurrence of pacer-mediated tachycardia, namely the repeated stimulation, as the result of retrograde conduction from the ventricle to the atrium, of an atrial event by a ventricular event a predetermined time interval after said ventricular event, said atrial stimulation being detected by said pacemaker causing said pacemaker to stimulate said ventricle after an atrio-ventricular delay, causing the just described cycle to repeat itself, on the detection of the presence of pacer-mediated tachycardia, automatically setting the post-ventricular atrial refractory period of the pacemaker at a magnitude greater than said predetermined time interval after the occurrence of a pulse in the ventricle, and latching said post-ventricular atrial refractory period of the pacemaker in at said magnitude during the continued operation of said pacemaker so that it can be changed only be external reprogramming to suppress pacer-mediated tachycardia during the continued operation following said setting.

2. The method of claim 1 including the step of automatically resetting the post-ventricular atrial refractory period to the magnitude greater than the time of retrograde conduction from the ventricle to the atrium on the occurrence of each ventricular event.

3. The method of claim 1 including the step of automatically resetting the post-ventricular atrial refractory period at a magnitude between 500 and 550 milliseconds.

4. The method of claim 1 wherein the monitoring for the occurrence of pacer-mediated tachycardia includes the steps of determining the interval between successive ventricular events and when it is determined that this interval is a minimum, counting the number of successive ventricular events separated by said minimum interval and if the count is at least a predetermined number, defining pacer-mediated tachycardia as detected.

5. The method of operating a cardiac pacemaker while said pacemaker is in a host, said pacemaker having leads connected to the atrium and to the ventricle and having means for controlling the supply of pulses through said leads to said atrium and ventricle, the said method being practiced while said pacemaker is in use in said host and comprising: normally operating said pacemaker in the DDD mode, automatically monitoring the operation of said pacemaker for the occurrence of pacer-mediated tachycardia, namely, the repeated stimulation of the atrium by a ventricular event a predetermined time interval after said ventricular event, as the result of retrograde conduction from the ventricle to the atrium, said atrial stimulation being detected by said pacemaker causing said pacemaker to stimulate said ventricle after an atrio-ventricular delay, causing the just described cycle to repeat itself on the detection of the presence of pacer-mediated tachycardia automatically setting the post-ventricular atrial refractory period of the pacemaker at a magnitude greater than said predetermined time interval after the occurrence of a pulse in the ventricle, maintaining said post-venticular atrial refractory period of the pacemaker at said magnitude during the continued operation of said pacemaker to suppress pacer-mediated tachycardia during the continued operation following said setting, at the same time changing the mode of operation of said pacemaker from DDD to DDT during said continued operation of said pacemaker thereby to trigger a zero delay spike on the manifestation of each event, to provide an indication of the occurrence of pacer-mediated tachycardia, and maintaining said pacemaker in said DDT mode.

6. The method of claim 5 wherein includes the additional step of increasing, by a relatively small magnitude, the minimum pacing rate of the pacemaker from the rate set prior to the detection of pacer-mediated tachycardia.

7. The method of claim 5 including the step of automatically resetting the post-ventricular atrial refractory period to the magnitude greater than the time of retrograde conduction from the ventricle to the atrium on the occurrence of each ventricular event.

8. The method of claim 5 including the step of automatically resetting the post-ventricular atrial refractory period at a magnitude between 500 and 550 milliseconds.

9. The method of claim 5 wherein the monitoring for the occurrence of pacer-mediated tachycardia includes the steps of determining the interval between successive ventricular events and when it is determined that this interval is a minimum counting the number of successive ventricular events separated by said minimum interval and if the count is at least a predetermined number, defining pacer-mediated tachycardia as detected.

10. The method of operating a cardiac pacemaker while said pacemaker is in a host, said pacemaker having leads connected to the atrium and to the ventricle, and having means for controlling the supply of pulses through said leads to said atrium and ventricle, the operation of said pacemaker being subject to pacer-mediated tachycardia, namely, the repeated stimulation of the atrium by a ventricular event a predetermined time interval after said ventricular event as the result of retrograde conduction from the ventricle to the atrium, said atrial stimulation being detected by said pacemaker causing said pacemaker to stimulate said ventricle after an atrio-ventricular delay, causing the just described cycle to repeat itself, the same pacemaker including the function of automatically terminating pacer-mediated tachycardia capable of being selectively programmed "off" or "on"; the said method being practiced while said pacemaker is in use in said host and including: normally operating said pacemaker in the DDD mode, programming said function of automatically terminating pacer-mediated tachycardia to "on", automatically monitoring the operation of said pacemaker for pace-mediated tachycardia, on the detection of the presence of pacer-mediated tachycardia automatically setting the post-ventricular atrial refractory period of the pacemaker at a magnitude greater than said predetermined time interval after the occurrence of an event in the ventricle, at the same time changing the mode of operation of said pacemaker from DDD to DDT thereby to trigger a zero-delay spike on each manifestation of an event, thereby to provide an indication of the occurrence of pacer-mediated tachycardia, and latching in the post-ventricular atrial refractory period at said greater magnitude and the operation of said pacemaker in the DDT mode so that said greater magnitude and said operation in the DDT mode are maintained during the continued operation of said pacemaker until changed by external reprogramming by a physician.

11. The method of claim 10 wherein the monitoring for the occurrence of pacer-mediated tachycardia includes the steps of determining the interval between successive ventricular events and when it is determined that this interval is a minimum counting the number of successive ventricular events separated by said minimum interval and if the count is at least a predetermined number, defining pacer-mediated tachycardia as detected.

12. A pacemaker for monitoring cardiac activity of the heart and for pacing the heat, said pacemaker being normally set to operate in the DDD mode, said pacemaker including a first electrode connected to the atrium of said heart, a second electrode connected to the ventricle of said heart, first pulsing means, connected to said first electrode, for impressing atrial pulses on said atrium, first sensing means connected to said first pulsing means and to said first electrode for inhibiting the impressing any atrial pulse on the occurrence of an intrinsic atrial event (herein "corresponding intrinsic atrial event"), pulsing means, connected to said second electrode, for impressing a ventricular pulse on said ventricle a predetermine time interval (herein "AV interval") after the impressing of an atrial pulse or the occurrence of a corresponding intrinsic atrial event, second sensing menas, connected to said second electrode and to said second pulsing means, for inhibiting the impressing of any ventricular pulse on the occurrence of an intrinsic ventricular event (herein "corresponding intrinsic ventricular event"), during said AV interval, timing means connected to said first and second pulsing means inhibiting the impressing of a succeeding atrial pulse a predetermined time interval (herein "PVARP") after the impressing intrinsic of said ventricular pulse or the occurrence of a corresponding ventricular event, means, connected to said first and second sensing means for detecting pacer-mediated tachycardia, namely, the repeated stimulation of the atrium by a said ventricular pulse or by a said corresponding intrinsic ventricular event a third predetermined time interval after said ventricular pulse or the occurrence of said corresponding intrinsic ventricular event as the result of retrograde conduction from said ventricle to said atrium, each said stimulation being manifested by the impressing of a pulse, by said first pulse-producing means through said first electrode on the atrium at the end of each said third interval, means for counting said stimulated pulses, resetting means, responsive to said counting means, after said counting means has counted a predetermined number of said stimulated pulses, for automatically setting PVARP to a greater time interval than said third interval thereby to suppress the impressing of said stimulated pulses and also for automatically resetting said pacemaker to DDT mode to superimpose a spike on each said atrial pulse or each said corresponding intrinsic atrial event and on each said ventricular pulse or on each said corresponding intrinsic ventricular event, and means, connected to said setting means, for latching in said setting of said PVARP to said greater time interval and the setting of said DDT mode so that they can only be reset by external programming means.

13. The pacemaker of claim 12 including means, connected to the resetting means, for programming said resetting means to an "on" condition in which said resetting means is enabled to carry out the resetting automatically or to an "off" condition in which the resetting means is disabled.

* * * * *